US006911080B2

United States Patent
Kishi et al.

(10) Patent No.: US 6,911,080 B2
(45) Date of Patent: Jun. 28, 2005

(54) EVALUATION PROCESS OF REACTIVITY OF SILICA GLASS WITH SILICON MELT AND VIBRATION AT ITS SURFACE, AND SILICA GLASS CRUCIBLE NOT CAUSING THE SURFACE VIBRATION

(75) Inventors: Hiroshi Kishi, Akita (JP); Minoru Kanda, Akita (JP); Masanori Fukui, Akita (JP)

(73) Assignee: Japan Super Quartz Corporation, Tokyo (JP)

( * ) Notice: Subject to any disclaimer, the term of this patent is extended or adjusted under 35 U.S.C. 154(b) by 36 days.

(21) Appl. No.: 10/682,112

(22) Filed: Oct. 10, 2003

(65) Prior Publication Data

US 2004/0118208 A1 Jun. 24, 2004

(30) Foreign Application Priority Data

Oct. 22, 2002 (JP) ....................................... 2002-307214

(51) Int. Cl.[7] ............................................. C30B 15/10
(52) U.S. Cl. ........................... 117/13; 117/14; 117/208; 117/900; 65/17.3; 65/17.4; 65/32.1
(58) Field of Search ............................. 117/13, 14, 208, 117/900; 65/17.3, 17.4, 32.1

(56) References Cited

U.S. PATENT DOCUMENTS

| 5,053,359 A | * | 10/1991 | Loxley et al. | .................. 501/4 |
| 5,609,682 A | * | 3/1997 | Sato et al. | ...................... 117/2 |
| 5,704,973 A | * | 1/1998 | Sakurada et al. | ............. 117/15 |
| 5,730,800 A | * | 3/1998 | Sato et al. | .................. 118/200 |
| 6,553,787 B1 | * | 4/2003 | Akiho et al. | ................. 65/17.3 |
| 6,652,934 B1 | * | 11/2003 | Miyao et al. | ............... 428/34.4 |
| 2003/0074920 A1 | * | 4/2003 | Ohama et al. | ............... 65/17.4 |

* cited by examiner

*Primary Examiner*—Robert Kunemund
(74) *Attorney, Agent, or Firm*—Oblon, Spivak, McClelland, Maier & Neustadt, P.C.

(57) ABSTRACT

A evaluation process of a vibration level at the surface of silicon melt held in a silica glass crucible is provided by setting in the vacuum furnace, the test piece of the silica glass cut out from a silica glass crucible, melting a little amount of silicon put on said piece of the glass, and measuring a vibration cycle of the silicon melt. Moreover, a silica glass crucible not causing the vibration at the surface of the silicon melt held in the silica glass crucible is also provided, wherein the vibration cycle of a silica glass of a side wall of the crucible is controlled at more than ⅙ seconds.

8 Claims, 1 Drawing Sheet

[Figure 1]
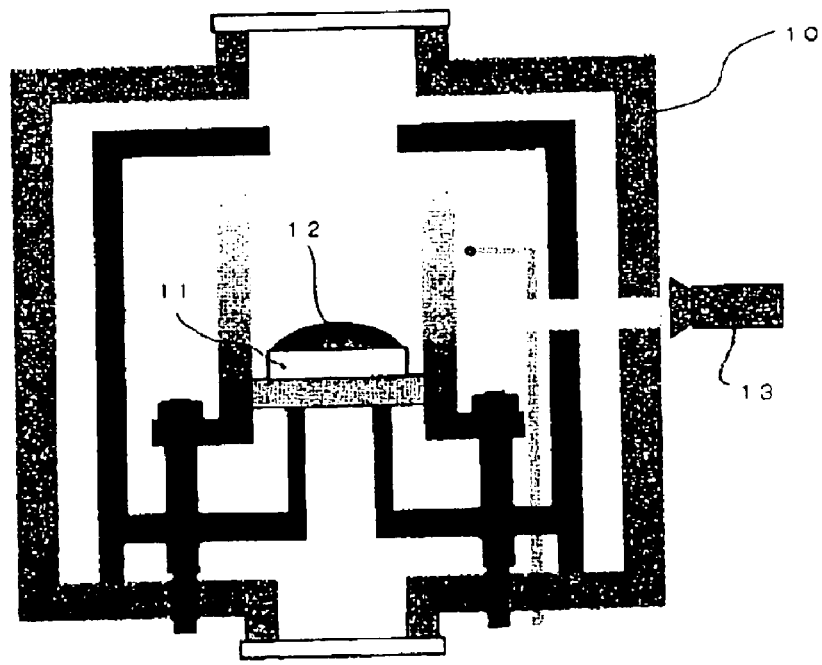
[Figure 2]
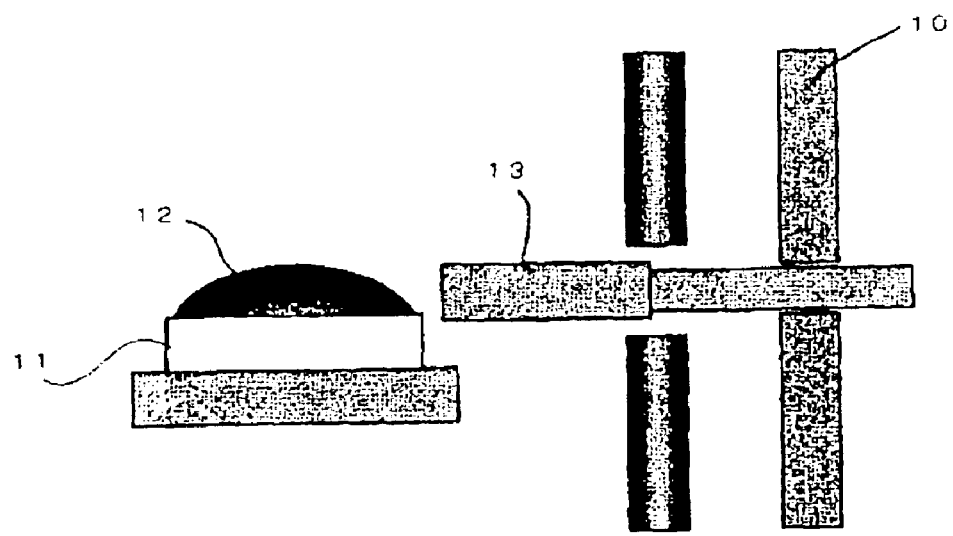

EVALUATION PROCESS OF REACTIVITY OF SILICA GLASS WITH SILICON MELT AND VIBRATION AT ITS SURFACE, AND SILICA GLASS CRUCIBLE NOT CAUSING THE SURFACE VIBRATION

BACKGROUND OF THE INVENTION

1. Field of the Invention

The present invention relates to a simple and sure evaluation process, by which a reactivity of a silica glass with silicon melt or a phenomenon of a vibration at the surface of the silicon melt held in a silica glass crucible can be evaluated. Furthermore, the present invention also relates to a silica glass crucible improved by applying said evaluation process. When the improved crucible is used for pulling silicon single crystal, a vibration at the surface of the silicon melt held in the crucible is remarkably suppressed.

2. Discussion of the Background

A silicon single crystal used as a raw material for a semiconductor silicon wafer has been produced mainly by Czochralsky (CZ) method. Since CZ method is the method of growing up the silicon single crystal, by contacting a single-crystal seed with the silicon melt held in the silica glass crucible, the crystallization of the silicon single crystal by CZ method is remarkably prevented by a phenomenon of the vibration at the surface of the silicon melt held in the silica glass crucible, and a yield of single crystal is decreased clearly. Hereinafter, the phenomenon is referred to as "the surface vibration of the silicon melt". Therefore, the silica crucible, which does not cause the surface vibration of the silicon melt, has been required strongly.

The surface vibration of the silicon melt is caused by the reaction of the silica glass with the silicon melt. However, conventionally, as for the silica glass crucible, any method for evaluating the vibration level at the surface of silicon melt held in a silica glass crucible has not yet been known, and there has been no method to evaluate whether a silica glass crucible causes the vibration or not, except that a pulling test of silicon single crystal is actually carried out by using said silica glass crucible. Moreover, as for the reactivity of the silica glass with the silicon melt, which causes the surface vibration of the silicon melt, many complicated factors are related, for example such as a dissolution speed of silica glass to silicon melt, a bubble content of the crucible, a various impurities concentrations in silica glass, and a roughness on the surface of silica glass, and it has not been confirmed correctly that how degrees of the influence are given to the reactivity by each factors. Therefore, in order to obtain the silica crucible not causing the surface vibration of the silicon melt, it is necessary to carry out the many pulling tests to evaluate the crucibles, and even if said pulling tests are repeated, it is difficult to obtain the silica crucible not causing the surface vibration of the silicon melt.

In such a prior circumstances, recently, a method has been disclosed as the method for evaluating the surface vibration of the silicon melt, wherein the method consisted of melting silicon on a silica glass sample piece and measuring the decreasing amount of the silica glass to estimate indirectly the surface vibration of the silicon melt (Japanese Patent Laid Open No. 2002-154894). However, as for this method, an error is much, so that it is difficult to obtain the result agreeing with the result of pulling actually. As described above, many factors, such as the dissolution speed of the silica glass, the bubble content of the crucible, the various impurities concentrations, and the roughness of the surface, are related complicatedly to the surface vibration of the silicon melt, so that, only with measuring the decreasing amount of the silica glass as disclosed by the above prior art, it is difficult to evaluate the surface vibration of the silicon melt.

SUMMARY OF THE INVENTION

The present invention solves such the conventional problems. Inventors focused on the vibration cycle of silicon melt on the silica glass sample piece and it was found out that the surface vibration of the silicon melt could be suppressed remarkably when the vibration cycle was more than a certain steady value. Based on this knowledge, the present invention provides the process, in which the surface vibration of the silicon melt can be evaluated easily and certainly, and provides the improved silica glass crucible based on this evaluation process.

That is, according to the present invention, the evaluation process for the reactivity of the silica glass and the surface vibration of the silicon melt and the silica glass crucible not causing the surface vibration of the silicon melt, are provided, as the following constitutions.

[1] An evaluation process for a reactivity of a silica glass with silicon melt, the method comprising;

melting a little amount of silicon on the test piece of the silica glass in a vacuum furnace, and measuring a vibration cycle of the silicon melt.

[2] An evaluation process for a vibration at a surface of the silicon melt held in a silica glass crucible, the method comprising;

setting in the vacuum furnace, the test piece of the silica glass cut out from a silica glass crucible, on which a little amount of silicon is put, melting the little amount of silicon on said test piece of the glass, and measuring the vibration cycle of the silicon melt.

[3] The evaluation process according to above [1] or [2], the process comprising;

adjusting an inside of the vacuum furnace to an argon pressure of from 5 to 100 torr and a temperature of from 1450 to 1600 degree C., melting a little amount of silicon on the test piece of the silica glass, and measuring the vibration cycle of the silicon melt.

[4] A silica glass crucible for pulling a silicon single crystal, wherein an inner surface of a side wall of the crucible comprises the silica glass not vibrating or vibrating in the vibration cycle more than ⅙ seconds in the evaluation process according to above [3].

[5] A silica glass crucible for pulling a silicon single crystal, wherein an inner surface of the side wall comprises the silica glass not vibrating or vibrating in the vibration cycle more than ⅙ seconds, and an inner surface of a bottom comprises the silica glass vibrating in the vibration cycle less than ⅙ seconds, in the evaluation process according to above [3].

According to the evaluation process of the present invention, the reactivity of the silica glass with the silicon melt can be evaluated easily and certainly. Therefore, the vibration level at the surface of the silicon melt held in the silica glass crucible can be estimated by using this evaluation process. That is, if the vibration cycle of the silicon melt on the test piece of a silica glass is measured by this evaluation process, the surface vibration level of the silicon melt in the crucible, which comprises the same kind of the silica glass as said test piece of the silica glass, can be estimated beforehand based on said measured vibration cycle of the test piece.

Furthermore, the silica glass crucible, in which the surface vibration of the silicon melt does not occur, can be manufactured by applying the vibration cycle value measured by the test piece. That is, the crucibles, which don't occur said surface vibration, can be easily manufactured by fixing the manufacturing conditions to the same, by which the silica glass crucible having a desired vibration cycle value is produced. Concretely, for example, the surface vibration cycle of the silicon melt held in the silica glass crucible is influenced also with the bubble content just under the surface of the silica glass, and is generally shorter as the bubble contents are increasing. Therefore, if the measured vibration cycle on the test piece of the silica glass is applied to the crucible producing process, the silica glass crucible having a comparatively long vibration cycle, i.e., a little vibration at the surface of the silicon melt, can be obtained by controlling the bubble content just under the surface of the silica glass, which is the same kind as said test piece of the silica glass.

It is very important that this invention has newly shown there is an optimum range of the bubble content just under the surface of the silica glass crucible, in order to decrease the surface vibration of the silicon melt.

BRIEF DESCRIPTION OF THE DRAWINGS

The advantages of the present invention may be better understood by reference to the drawings, wherein:

FIG. 1 shows the schematic figure showing an embodiment of a evaluation process of the present invention.

FIG. 2 shows the enlarged figure showing a measuring state of a silicon melt on a piece of a glass in the FIG. 1.

The description of the main cords is as follows,

10—Vacuum furnace, 11—Piece of a silica glass, 12—Silicon melt, and 13—Optical measuring means

DETAILED DESCRIPTION OF THE PREFERRED EMBODIMENT

Hereinafter, the present invention will be explained concretely with the preferred embodiment.

The evaluation process of the present invention is the evaluation process of the reactivity of the silica glass with the silicon melt, the process comprising; melting a little amount of silicon on the test piece of the silica glass in the vacuum furnace, and measuring the vibration cycle of the silicon melt. In addition, as for the silica glass crucible, the present invention is the evaluation process of the surface vibration of the silicon melt, the method comprising; setting the test piece of the silica glass cut out from a silica glass crucible in the vacuum furnace, melting a little amount of silicon on said piece of the silica glass, and measuring the vibration cycle of the silicon melt.

As for the condition of said evaluation process, it is preferable that high purity silicon from 2 to 20 g is used, the inside of the vacuum furnace is adjusted to the argon pressure of from 5 to 100 torr, and the temperature of from 1450 to 1600 degree C. More particularly, it is preferable that the vibration of the silicon melt on the piece of the silica glass is measured under the conditions of silicon amount of 10 g, the argon pressure of 20 torr, and the temperature of 1560 degree C.

An example of the measuring equipment of said evaluation process is shown in FIG. 1 and FIG. 2. As shown in the drawings, the test piece of the silica glass 11 is set in the vacuum furnace 10, and the atmosphere and temperature in the furnace are adjusted to above-described conditions. A silicon block put on the test piece of said silica glass is melted, and the vibration cycle of the silicon melt is measured by visual observation through an optical measuring means 13 extending to the side of the silicon melt 12.

The vibration cycle of the silicon melt on the test piece is varied with the level of the reactivity of the silica glass with the silicon melt. Therefore, the reactivity of the silica glass with the silicon melt can be evaluated by the vibration cycle.

Furthermore, the vibration level at the surface of the silicon melt held in the silica glass crucible can be evaluated too, by measuring the vibration cycle of the silicon melt on the piece of silica glass. The influence of a silica glass quality to the surface vibration of the silicon melt is not uniform in each portion of the silica glass crucible, and the influence of the side wall of the crucible is large. Therefore, as for the silica glass of the side wall of the crucible, a such silica glass as the vibration of the silicon melt on the test piece of the silica glass is not occurred as much as possible, is preferable.

More particularly, as for the silica glass crucible for pulling up silicon single crystal, the silica glass crucible, in which the side wall of the crucible is formed with the following silica glass, is preferable. As for said silica glass, the silicon melt on the test piece of the silica glass is not vibrated or vibrated in the vibration cycle as more than $\frac{1}{6}$ seconds, when the test piece of the silica glass cut out from the silica glass crucible is set in the vacuum furnace and a little amount of silicon, i.e., from 2 to 20 g, on the test piece of the silica glass is melted by heating under the argon pressure of from 5 to 100 torr and the temperature of from 1450 to 1600 degree C., wherein, most preferably, the silicon amount is 10 g, the argon pressure in the furnace is 20 torr, and the temperature in the furnace is 1560 degree C. When the silica glass crucible having the side wall formed with silica glass, the silicon melt on the test piece of which vibrates in the vibration cycle shorter than $\frac{1}{6}$ seconds, is used for pulling up silicon single crystal, much vibration occurs at the surface of the silicon melt, so that the dislocation in the single crystal is occurred. On the other hand, when the silica glass crucible having the side wall formed with the silica glass, the silicon melt on the test piece of which does not vibrate or vibrates in the longer cycle than $\frac{1}{6}$ seconds, is used for said pulling process, the surface vibration of the silicon melt is not occurred at the pulling, or it is very weak even if said vibration is occurred, so that said vibration does not influence to the quality of the obtained silicon single crystal.

On the other hand, an influence of the quality of the silica glass at the bottom of the crucible to the surface vibration of the silicon melt is very low, since the bottom of the crucible is far from the surface of the silicon melt held in the silica glass crucible and the vibration itself at the bottom portion is suppressed by heavy weight of the silicon melt, so that the quality of the silica glass at the bottom of the crucible does not influence to the surface vibration of the silicon melt. However, the quality influences to the dislocation free ratio of the silicon single crystal at pulling. That is, when the bottom of the crucible is formed with the silica glass, wherein the vibration cycle of the silicon melt on the test piece of the silica glass is shorter than $\frac{1}{6}$ seconds, the dislocation free ratio of the silicon single crystal at pulling, is sufficient.

EXAMPLE

Hereinafter, the present invention is further explained by way of the concrete examples.

Example 1

According to the evaluation process of this invention, the vibration level at the surface of the silicon melt held in the silica glass crucible was evaluated. The several kinds of the silica glass crucible having the different qualities were used for the measurement, wherein the standard size of those crucibles was 28 inches of an open diameter and from 11 to 13 mm of the thickness of side wall. First, the piece of the glass (30 mm×30 mm) was cut out from the side wall of the crucible and was set in the vacuum furnace as shown in FIG. 1. Next, 10 g of high purity silicon was put on said test piece of the silica glass, and the inside of the furnace was adjusted to the argon pressure of 20 torr and the temperature of 1560 degree C., and the silicon on the piece of the glass was melted. Then, the vibration cycle of the silicon melt was measured by visual observation. The measured results are shown in Table 1. Furthermore, by using each two silica glass crucibles having same quality as the test piece of the measured silica glass, the silicon single crystal was actually pulled up and the results are also shown in Table 1.

It is clearly shown by the results (No. 1 to No. 4), that when the silicon melt on the test piece of the silica glass cut out from the side wall of the crucible was not vibrated or vibrated in the vibration cycle of longer than $\frac{1}{6}$ seconds, the surface vibration of the silicon melt was not occurred at the pulling, or it was very weak even if said vibration was occurred. Therefore there were no problems, and further, the dislocation was not occurred in the pulled silicon single crystal.

On the other hand, it is shown by the results (No. 5 to No. 8), that when the silicon melt on the piece of the silica glass cut out from the side wall of the crucible was vibrated in the vibration cycle of shorter than $\frac{1}{6}$ seconds, the vibration cycle at the surface of the silicon melt held in the each silica glass crucible was large at the pulling, so that the dislocation was occurred in the pulled silicon single crystal, and further, dislocation free ratio of silicon single crystal became to be low.

Example 2

According to the evaluation process of this invention, the vibration level at the surface of the silicon melt held in the silica glass crucible was evaluated. The several kinds of the silica glass crucible having the different qualities were used for the measurement, wherein the standard size of those crucibles was 28 inches of an open diameter and from 12 to 15 mm of the bottom thickness. First, the piece of the glass (30 mm×30 mm) was cut out from the bottom of the crucible and was set in the vacuum furnace as shown in FIG. 1. Then, the vibration cycle of the silicon melt was measured under the same condition as Example 1. The measured results are shown in Table 2. Furthermore, by using each two silica glass crucibles having same quality as the test piece of the measured silica glass, the silicon single crystal was actually pulled up and the results are also shown in Table 2.

It is clearly shown by the results (No. 9 to No. 16), that even when the silicon melt on the test piece of the silica glass cut out from the bottom of the crucible was vibrated in the vibration cycle of shorter than $\frac{1}{6}$ seconds, the surface vibration of the silicon melt was not occurred at the pulling, or it was very weak even if said vibration was occurred. Therefore there were no problems, and further, the dislocation was not occurred in the pulled silicon single crystal.

However, as for the dislocation free ratio of silicon single crystal, it was confirmed to be related with the vibration cycle of the silicon melt on the test piece, and the silica glass crucibles (No. 12 to No. 16), in which the vibration cycle were shorter than $\frac{1}{6}$ seconds, were more sufficient than the other silica glass crucibles in the dislocation free ratio of the silicon single crystal.

According to the evaluation process of the present invention, the level of the surface vibration of the silicon melt can be evaluated easily and certainly by measuring the vibration cycle of the silicon melt on the test piece of the silica glass. Therefore, by using said evaluation process, the level of the surface vibration of the silicon melt can be evaluated without carrying out the actual pulling test of the single crystal.

It is very important that this invention has newly shown that, in order to decrease the surface vibration of the silicon melt, there is an optimum range of the bubble content of just under the surface of the silica glass crucible, in each section such as wall or bottom of its inner surface.

TABLE 1

| No. | Vibration cycle of Silicon melt on a Piece of Glass of Side Wall of Crucible | Vibration at the Surface of the Silicon melt at Pulling up | Occurring of Dislocation in Silicon Single Crystal | Dislocation Free Ratio |
|---|---|---|---|---|
| 1 | More Than 10 seconds | Very Weak Vibration (Not Influenced) | Not Occurred | 84 |
|   |   |   | Not Occurred | 83 |
| 2 | 1 second | Very Weak Vibration (Not Influenced) | Not Occurred | 81 |
|   |   |   | Not Occurred | 80 |
| 3 | $\frac{1}{3}$ seconds | Very Weak Vibration (Not Influenced) | Not Occurred | 77 |
|   |   |   | Not Occurred | 77 |
| 4 | $\frac{1}{6}$ seconds | Very Weak Vibration (Not Influenced) | Not Occurred | 71 |
|   |   |   | Not Occurred | 72 |
| 5 | $\frac{1}{7}$ seconds | Little Large Vibration (Influenced) | Occurred | 49 |
|   |   |   | Occurred | 51 |
| 6 | $\frac{1}{8}$ seconds | Little Large Vibration (Influenced) | Occurred | 44 |
|   |   |   | Occurred | 40 |
| 7 | $\frac{1}{10}$ seconds | Little Large Vibration (Influenced) | Occurred | 28 |
|   |   |   | Occurred | 34 |
| 8 | $\frac{1}{20}$ seconds | Large Vibration (Influenced Remarkably) | Occurred | 14 |
|   |   |   | Occurred | 10 |

TABLE 2

| No. | Vibration Cycle of Silicon melt on a Piece of Glass of Bottom Wall of Crucible | Vibration at the Surface of the Silicon melt at Pulling up | Occurring of Dislocation in Silicon Single crystal | Dislocation Free Ratio |
|---|---|---|---|---|
| 9 | More Than 10 seconds | Very Weak Vibration (Not Influenced) | Not Occurred | 42 |
|   |   |   | Not Occurred | 44 |
| 10 | 1 second | Very Weak Vibration (Not Influenced) | Not Occurred | 46 |
|   |   |   | Not Occurred | 48 |
| 11 | $\frac{1}{3}$ seconds | Very Weak Vibration (Not Influenced) | Not Occurred | 51 |
|   |   |   | Not Occurred | 51 |
| 12 | $\frac{1}{6}$ seconds | Very Weak Vibration (Not Influenced) | Not Occurred | 65 |
|   |   |   | Not Occurred | 63 |

TABLE 2-continued

| No. | Vibration Cycle of Silicon melt on a Piece of Glass of Bottom Wall of Crucible | Vibration at the Surface of the Silicon melt at Pulling up | Occurring of Dislocation in Silicon Single crystal | Dislocation Free Ratio |
|---|---|---|---|---|
| 13 | 1/7 seconds | Very Weak Vibration | Not Occurred | 69 |
|  |  | (Not Influenced) | Not Occurred | 72 |
| 14 | 1/8 seconds | Very Weak Vibration | Not Occurred | 75 |
|  |  | (Not Influenced) | Not Occurred | 76 |
| 15 | 1/10 seconds | Very Weak Vibration | Not Occurred | 83 |
|  |  | (Not Influenced) | Not Occurred | 81 |
| 16 | 1/20 seconds | Very Weak Vibration | Not Occurred | 85 |
|  |  | (Not Influenced) | Not Occurred | 85 |

What is claimed is:

1. An evaluation process of a reactivity of a silica glass with silicon melt, the process comprising;

melting a little amount of silicon on the test piece of the silica glass in a vacuum furnace, and measuring a vibration cycle of the silicon melt.

2. The evaluation process of claim 1, the process comprising;

adjusting an inside of the vacuum furnace to an argon pressure of from 5 to 100 torr and a temperature of from 1450 to 1600 degree C., melting a little amount of silicon on the piece of the silica glass, and measuring the vibration cycle of the silicon melt.

3. An evaluation process of a vibration at a surface of a silicon melt held in a silica glass crucible, the process comprising;

setting in the vacuum furnace, the test piece of the silica glass cut out from a silica glass crucible, on which a little amount of silicon is put, melting the little amount of silicon on said test piece of the silica glass, and measuring the vibration cycle of the silicon melt.

4. The evaluation process of claim 3, the process comprising;

adjusting an inside of the vacuum furnace to an argon pressure of from 5 to 100 torr and a temperature of from 1450 to 1600 degree C., melting a little amount of silicon on the test piece of the silica glass, and measuring the vibration cycle of the silicon melt.

5. A silica glass crucible for pulling a silicon single crystal, wherein an inner surface of a side wall comprises the silica glass not vibrating or vibrating in the vibration cycle more than 1/6 seconds in the evaluation process according to claim 4.

6. A silica glass crucible for pulling a silicon single crystal, wherein an inner surface of the side wall comprises the silica glass not vibrating or vibrating in the vibration cycle more than 1/6 seconds and the inner surface of a bottom comprises the silica glass vibrating in the vibration cycle less than 1/6 seconds, in the evaluation process according to claim 4.

7. A process for preparing a silicon single crystal by Czochralsky method, the process comprising;

loading polycrystalline silicon into a silica glass crucible, wherein an inner surface of the side wall comprises the silica glass not vibrating or vibrating in the vibration cycle more than 1/6 seconds in the evaluation process according to claim 4, melting the polycrystalline silicon within the silica glass crucible and pulling up a silicon single crystal from the obtained silicon melt by using a single-crystal seed.

8. A process for preparing a silicon single crystal by Czochralsky method, the process comprising;

loading polycrystalline silicon into a silica glass crucible, wherein an inner surface of the side wall comprises the silica glass not vibrating or vibrating in the vibration cycle more than 1/6 seconds, and an inner surface of the bottom comprises the silica glass vibrating in the vibration cycle less than 1/6 seconds, in the evaluation process according to claim 4, melting the polycrystalline silicon within the silica glass crucible and pulling up a silicon single crystal from the obtained silicon melt by using a single-crystal seed.

* * * * *